(12) United States Patent
Tsujii

(10) Patent No.: US 6,911,988 B1
(45) Date of Patent: Jun. 28, 2005

(54) APPARATUS, METHOD AND MEMORY MEDIUM FOR PROCESSING A RADIATION IMAGE

(75) Inventor: Osamu Tsujii, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 372 days.

(21) Appl. No.: 09/717,045

(22) Filed: Nov. 22, 2000

(30) Foreign Application Priority Data

Nov. 26, 1999 (JP) ............................................ 11-336160

(51) Int. Cl.⁷ .............................................. G09G 5/00
(52) U.S. Cl. ........................ 345/581; 382/132; 378/206
(58) Field of Search ........................... 345/581; 382/132

(56) References Cited

U.S. PATENT DOCUMENTS

| | | | |
|---|---|---|---|
| 4,851,701 A | | 7/1989 | Nakajima ................. 250/327.2 |
| 4,903,310 A | | 2/1990 | Takeo et al. .................... 382/6 |
| 4,951,201 A | | 8/1990 | Takeo et al. ........... 364/413.13 |
| 5,172,419 A | * | 12/1992 | Manian ....................... 382/132 |
| 5,579,402 A | * | 11/1996 | Hayen ......................... 382/132 |
| 5,628,039 A | | 5/1997 | Muramatsu et al. ......... 396/276 |
| 5,862,249 A | * | 1/1999 | Jang et al. ................... 382/132 |
| 6,314,198 B1 | * | 11/2001 | Ogura ......................... 382/132 |
| 6,317,510 B1 | * | 11/2001 | Murakami ................... 382/132 |
| 8,313,477 | * | 11/2001 | Yasuda et al. ............... 250/587 |
| 6,411,674 B1 | * | 6/2002 | Oikawa ......................... 378/21 |
| 6,415,049 B1 | * | 7/2002 | Yanagita et al. ............. 382/132 |
| 6,501,827 B1 | * | 12/2002 | Takasawa ................... 378/116 |
| 6,502,984 B2 | * | 1/2003 | Ogura et al. ................. 378/206 |

FOREIGN PATENT DOCUMENTS

| | | |
|---|---|---|
| JP | 55-12429 | 1/1980 |
| JP | 56-11395 | 2/1981 |
| JP | 6-77579 | 10/1994 |
| JP | 6-93076 | 11/1994 |
| JP | 10-243456 | 9/1998 |
| JP | 11-89823 | 4/1999 |

OTHER PUBLICATIONS

A.K. Jain, "Fundamentals of Digital Image Processing", University of California, Davis, Prentice–Hall, Inc., (1989).

* cited by examiner

Primary Examiner—Michael Razavi
Assistant Examiner—Jin-Cheng Wang
(74) Attorney, Agent, or Firm—Fitzpatrick, Cella, Harper & Scinto

(57) ABSTRACT

From a taken image such as a radiation image, plural characteristic amounts (two-dimensional characteristic amounts etc.) are extracted to judge the portion (position) of the object on the taken image, and the result of judgment is displayed. On the image displaying the result of judgment of the object position, the operator confirms whether the object position is correctly judged, and, if the result is erroneous, changes the result of judgment by changing means. Based on the result of judgment changed by the operator or without such change, corresponding image processing parameters are acquired from the parameter table prepared in advance. Such image processing parameters are used for executing the image processing on the taken image.

13 Claims, 11 Drawing Sheets

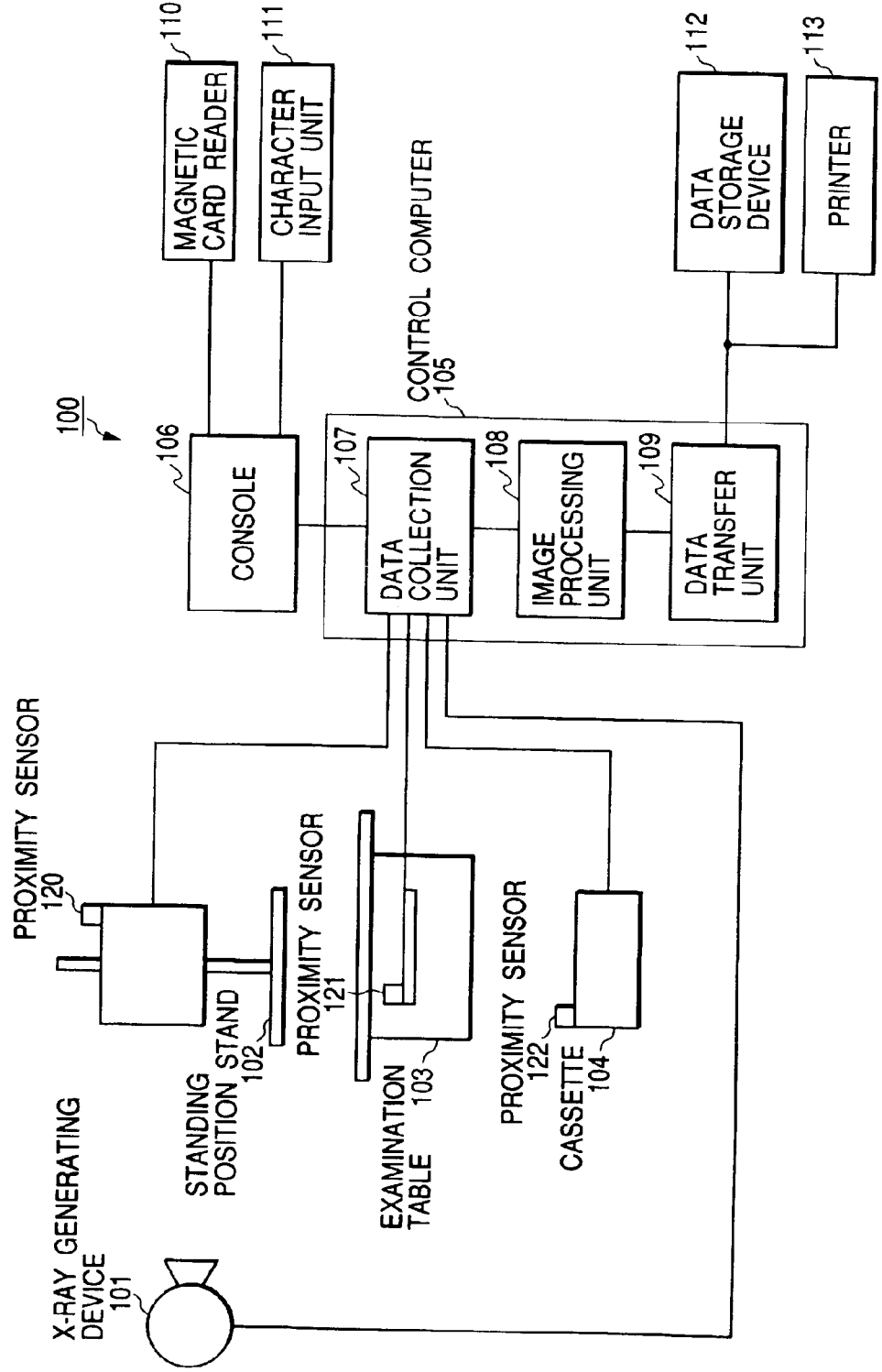

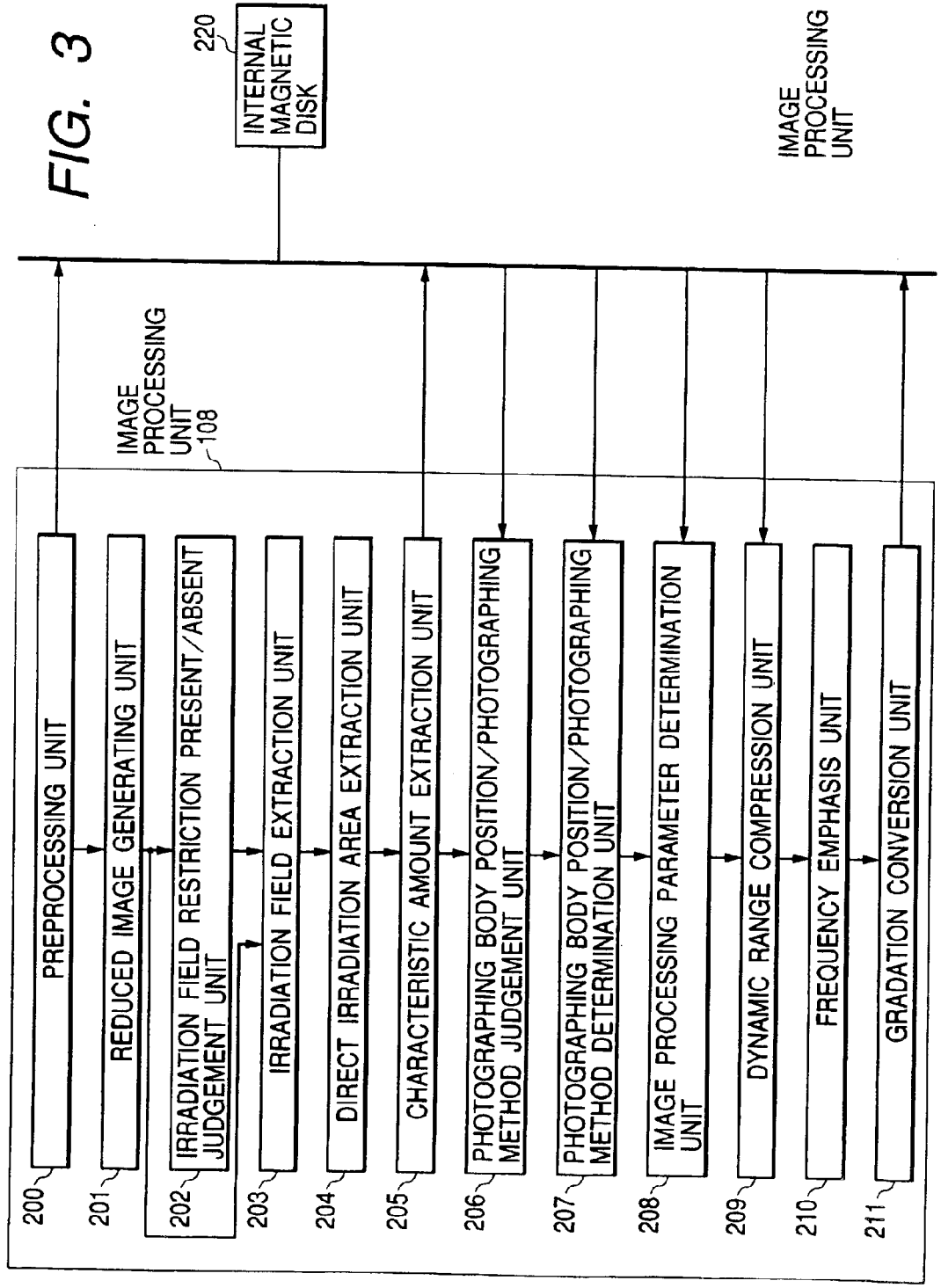

FIG. 6

| | HD CURVE TYPE | GAMMA | CENTER DENSITY | FREQUENCY EMPHASIS PATTERN | DRC PATTERN |
|---|---|---|---|---|---|
| CHEST REGION FRONT | 1 | 2.88 | 1.8 | 1 | 1 |
| CHEST REGION SIDE | 1 | 2.88 | 1.4 | 1 | 2 |
| CERVICAL VERTEBRAE FRONT | 2 | 4 | 1.6 | 3 | 3 |
| CERVICAL VERTEBRAE SIDE | 2 | 4 | 1.6 | 3 | 3 |
| ABDOMINAL REGION FRONT | 1 | 2.88 | 1.4 | 2 | 2 |
| ABDOMINAL REGION SIDE | 1 | 2.88 | 1.4 | 2 | 2 |
| SHOULDER FRONT | 2 | 4 | 1.5 | 3 | 3 |
| SHOULDER AXIS | 2 | | 1.4 | 3 | 3 |
| ANCON FRONT | 2 | 4 | 1.2 | 3 | 3 |

FIG. 12A

KAORU HARUNA : ESTHETIC SURGERY : THORACIC FRONT
TARO AKIBA : RESPIRATORY : CHEST RESGION FRONT
RYOU NATUKI : NOSE AND EARS : HEAD SIDE
REIKO TOUDO : GYNECOLOGY : LUMBAR VERTEBRA FRONT

PLEASE SELECT PATIENT

FIG. 12B

PATIENT NAME : KAORU HARUNA

PLEASE PHOTOGRAPH USING EXPOSURE BUTTON

[FINISH]

FIG. 12C

PATIENT NAME : TARO AKIBA

[IMAGE 1]

IT WAS THORACIC SPAIN FRONT IMAGE

PLEASE PHOTOGRAPH USING EXPOSURE BUTTON

2010 — [BODY POSITION CORRECTION] [IMAGE ADJUSTMENT] [FINISH]

FIG. 12D

PATIENT NAME : TARO AKIBA

[IMAGE 1] [IMAGE 2]

IT WAS THORACIC SPAIN SIDE IMAGE

PLEASE PHOTOGRAPH USING EXPOSURE BUTTON

[BODY POSITION CORRECTION] [IMAGE ADJUSTMENT] [FINISH]

FIG. 13A

KAORU HARUNA : ESTHETIC SURGERY : THORACIC FRONT
TARO AKIBA : RESPIRATORY : CHEST RESGION FRONT
RYOU NATUKI : NOSE AND EARS : HEAD SIDE
REIKO TOUDO : GYNECOLOGY : LUMBAR VERTEBRA FRONT

PLEASE SELECT PATIENT

FIG. 13B

PATIENT NAME : KAORU HARUNA
■ THORACIC SPAIN FRONT
☐ THORACIC SPAIN SIDE

PLEASE PHOTOGRAPH EXPOSURE BUTTON AFTER SELECTING PHOTOGRAPHING POSITION

[FINISH]

FIG. 13C

PATIENT NAME : TARO AKIBA

[IMAGE 1]

IT WAS JUDGED AS THORACIC SIDE IMAGE
■ THORACIC SPAIN FRONT
PLEASE PHOTOGRAPH USING EXPOSURE BUTTON

2010 — [BODY POSITION CORRECTION] [IMAGE ADJUSTMENT] [FINISH]

FIG. 13D

PATIENT NAME : TARO AKIBA

[IMAGE 1] [IMAGE 2]

IT WAS THORACIC SPAIN SIDE IMAGE

PLEASE PHOTOGRAPH USING EXPOSURE BUTTON

2010 — [BODY POSITION CORRECTION] [IMAGE ADJUSTMENT] [FINISH]

APPARATUS, METHOD AND MEMORY MEDIUM FOR PROCESSING A RADIATION IMAGE

BACKGROUND OF THE INVENTION

1. Field of the Invention

The present invention relates to an image processing apparatus capable of image processing such as gradation conversion utilizing image processing parameters based on characteristic values of an image taken for example with a radiation (such as X-ray).

2. Related Background Art

Certain luminescent substances, when subjected to radiation (X-ray, α-ray, β-ray, γ-ray, electron beam, ultra violet light etc.), accumulates a part of the energy of the radiation. Such luminescent substance, in a state of storing a part of the radiation energy, when irradiated with exciting light such as visible light, emits exhaustive light emission. The luminescent substance showing such property is called "photostimulable luminescent material".

As the image pickup apparatus utilizing such photostimulable luminescent material, a radiation image information record/reproducing apparatus is disclosed for example in the Japanese Patent Application Laid-open Nos. 55-12429 and 56-11395.

In such radiation image information record/reproducing apparatus (hereinafter called "radiation photographing apparatus 1"), the radiation image information (for example X-ray image information) of an object such as a human body is once recorded on a sheet of the photostimulable luminescent material (photostimulable luminescent sheet). Then such photostimulable luminescent sheet is scanned with exciting light such as a laser beam to generate exhaustive luminescent light from the sheet and the generated exhaustive luminescent light is photoelectrically read to obtain an image signal. The obtained image signal is subjected to image processing such as gradation conversion, and thus processed image signal is outputted, in a visible form of the radiation image of the object, to a recording medium such as a photosensitive material or a display device such as CRT.

Also there is recently developed a photographic apparatus (hereinafter called "radiation photographing apparatus 2") utilizing a semiconductor sensor to obtain the radiation image (X-ray image etc.) of the object in a similar manner as in the radiation photographing apparatus 1.

In comparison with the photographing apparatus (photoradiographic system) utilizing the conventional silver halide photographic technology, the above-mentioned radiation photographing apparatus 1 or 2 has a practical advantage capable of recording an image over an extremely wide radiation dose range.

More specifically, the radiation photographing apparatus 1 or 2 can acquire a radiation image not affected by the variation in the radiation dose, by converting the radiation, such as X-ray, of a very wide dynamic range after passing the object into an electrical signal by a sensor (photoelectric conversion means), and outputting the electrical signal after image processing to a recording medium such as a photographic sensitive material or a display device such as a CRT.

In such radiation photographic apparatus 1 or 2, it is required to automatically determine the parameters (image processing parameters) to be used for the image processing such as gradation conversion, in order to obtain the image of a density suitable for image observation (for example diagnostic observation by the doctor).

In general, the image processing parameters are classified into those dependent on the pattern of the photographed image (e.g., the photographing method, such as lateral chest photographing or thoracic vertebrae photographing; hereinafter also called "image pattern" or "photographing position"), and those not dependent on such image pattern. An example of a parameters dependent on the image pattern is the shift amount of the gamma curve upon graduation conversion, and an example of a parameters not dependent on the image pattern is the contrast of the gamma curve upon gradation conversion.

For example, it is desired, for the diagnosis of an image obtained by photographing a body portion from chest to lung (lung image), to execute the gradation conversion so as to obtain a gamma value of about 2.88. On the other hand, for an image obtained by lateral chest photographing of thoracic vertebrae (thoracic vertebrae image), it is desired for the diagnostic purpose to execute the gradation conversion so as to obtain a gamma value of about 4.

Therefore, in order to obtain a photographed image suitable for the diagnostic purpose, it is necessary, prior to the photographing or image processing, to acquire the information on the image pattern (photographing position) for example whether the intended image is a lung image or a thoracic vertebrae image.

Such information may be acquired by input by the user into the photographing apparatus (manual input method) or by automatic computer calculation in the photographing apparatus (photographing position judging method by a photographing position recognition program) without the manual input. For judging the photographing position of the medical image, there is known radiation image information reading methods as disclosed in the Japanese Patent Publications Nos. 06-077571 to 06-077579 and 06-093076.

However, the above-mentioned conventional photographing position judging methods are to judge the photographing position of the object image based on the characteristics of an accumulated histogram obtained from the images of different photographing positions or of accumulated profiles in the X and Y direction in the central portion of the image, and can only provide one-dimensional characteristic amounts for judging the photographing position since such accumulated histogram accumulated profile is obtained by converting a two-dimensional object image into one-dimensional information. Such characteristic amount is insufficient for judging the photographing position of the two-dimensional object image.

Also the judgment of the photographing position itself is rather simple (for example judging the front or side of the chest), and it has been impossible to finely judge the photographing position.

Also in the above-described photographing apparatus utilizing the photostimulable luminescent material, a cassette (IP) of the photostimulable luminescent material bearing the image has to be correlated with the object (patient etc.) by the assistance of an operator (radiologist or radiological technician (for example by a bar code reader), and the photographing position may be entered by the operator at such assisting operation. Such operation is very inefficient.

On the other hand, in a DR (direct radiology) system utilizing a semiconductor sensor, if the object information is once entered (patient registration) by the operator into the system, the image and the object are correlated without any intervention of the operator thereafter.

In the photographing apparatus of the DR system, it is strongly desired to execute the automatic judgment of the photographing position at a high precision, and to effectively utilize the result of such judgment.

However, as explained in the foregoing, the conventional judging methods for the photographing position are inadequate for judging the photographing position of the two-dimensional object image, and it has been not possible to realize the highly precise judgment of the photographing position since the judgment itself is rather simple.

SUMMARY OF THE INVENTION

An object of the present invention is to provide an image processing apparatus free from the aforementioned drawbacks and a control method therefor.

Another object of the present invention is to provide an image processing apparatus capable of applying optimum image processing to the object image thereby obtaining a satisfactory processed image even in case the photographing position of the object image cannot be judged precisely and efficiently, and a control method therefor.

Still another object of the present invention is to provide an image processing apparatus capable of easily correcting the automatically judged photographing position of the object image.

Still other objects of the present invention, and the features thereof, will become fully apparent from the following description to be taken in conjunction with the accompanying drawings and from the appended claims.

BRIEF DESCRIPTION OF THE DRAWINGS

FIG. 1 is a block diagram showing the configuration of a photographing system embodying the present invention;

FIG. 3 is a block diagram showing the configuration of an image processing unit in the above-mentioned photographing system;

FIG. 6 is a view showing an example of an image processing parameter table to be used in the above-mentioned image processing unit;

FIGS. 12A, 12B, 12C and 12D are views showing display images on a console in a 2nd embodiment; and FIGS. 13A, 13B, 13C and 13D are views showing display images on a console in a fourth embodiment.

DETAILED DESCRIPTION OF THE PREFERRED EMBODIMENTS

Figure 2A:
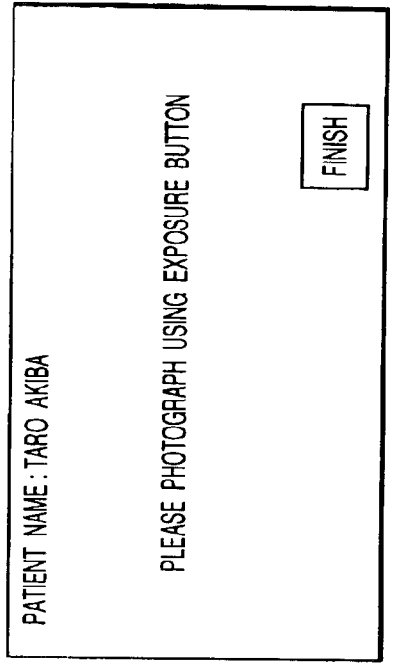
FIGS. 2A, 2B, 2C and 2D are views showing display images on a console of the above-mentioned photographing system.

In the following, the present invention will be clarified in detail by preferred embodiments thereof, with reference to the accompanying drawings.

First Embodiment

The present invention is applicable to a photographing system 100 as shown in FIG. 1.

The photographing system 100 is provided with an X-ray generation device 101 for generating X-ray, a standing position stand sensor 102 for executing X-ray photographing while an object (patient) in a standing position, an examination table sensor 103 for executing X-ray photographing while the object (patient) is in a lying position, a cassette sensor 104 for executing X-ray photographing of a part (for example knee) of the object (patient), a computer 105 for processing the information obtained by the standing position stand sensor 102, the examination table sensor 103 and the cassette sensor 104, a console 106 for displaying for example the information after being processed by the computer 105, a magnetic card reader 110 for reading the recorded content of a magnetic card for fetching into the present system, a character input unit 111 for entering various information and instructions into the present system, a data storage device 112 for storing for example information after processing by the computer 105, and a printer 113 for printing for example the information after processing by the computer 105.

The standing position stand sensor 102, the examination table sensor 103 and the cassette sensor 104 are respectively provided with proximity sensors 120, 121, 122.

The computer 105 includes a data collection unit 107, an image processing unit 108 and a data transfer unit 109.

Entire Function of the Photographing System 100

The photographing system 100 is installed for example in an X-ray photographing room of a hospital, and functions in the following manner.

At first the patient visits the photographing room with a photographing request form. In this state, the console 6 displays an image indicating a state awaiting the registration of the patient, as shown in FIG. 2A.

Then the patient (or manager of the photographing system 100) inserts a hospital card, bearing a magnetic stripe and carried by the patient, into the magnetic card reader 110.

Figure 2B:
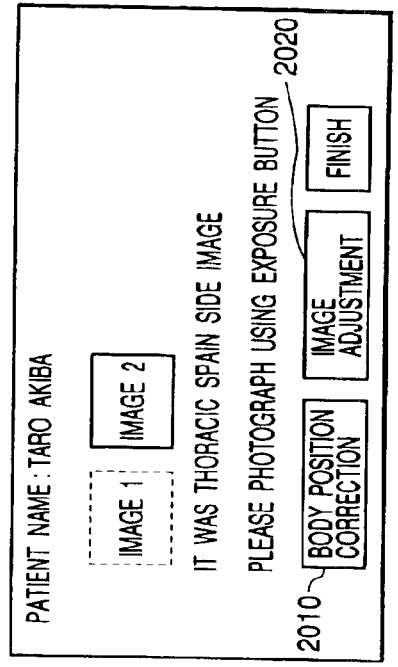

The magnetic card reader 110 scans the magnetic stripe of the inserted hospital card to read therefrom the patient information (name, birth date etc. of the patient). The read information (patient information) is supplied to the console 106. In response, the console 106 displays an image indicating that photographing system 100 is capable of photographing, as shown in FIG. 2B.

In the foregoing, the patient information is fetched into the photographing system 100 (patient registration) by the insertion of the hospital card, carried by the patient, into the magnetic card reader 110, but such form is not restrictive and the patient registration may be achieved by the entry of the patient information into the character input unit 111 by the manager of the photographing system 100.

After the patient registration is completed in this manner, the manager (for example radiologist or technician, hereinafter called "operator") of the photographing system 100 sets a portion to be photographed of the patient on the standing position stand sensor 102, the examination table sensor 103 or the cassette sensor 104 and depresses an unrepresented irradiation button, whereby the X-ray generation unit 101 generates X-ray to execute X-ray photographing of the patient.

In the photographing system 100, it is possible to recognize whether the portion to be photographed of the patient is set on the standing position stand sensor 102, the examination table sensor 103 or the cassette sensor 104 for example by providing each of such sensors with a manual switch for indicating the setting of the patient portion to be photographed and detecting the manipulation of these switches.

In the present embodiment, however, the standing position stand sensor 102, the examination table sensor 103 and the cassette sensor 104 are respectively provided with proximity sensors 120, 121, 122 as shown in FIG. 1, and these proximity sensors are utilized for recognizing the sensor on which the patient portion to be photographed is set. In this manner there can be dispensed with the aforementioned switching operation by the operator.

More specifically, if the patient stands in front of the standing position stand sensor 102 for the purpose of chest front photographing, the presence of the patient is detected by the proximity sensor 120 of the standing position stand sensor 102. Then, if the patient lies on the examination table 103 for the purpose of abdominal front photographing, the presence of the patient is detected by the proximity sensor 121 of the examination table sensor 103. Also, if the knee of the patient is positioned in front of the cassette sensor 104 for the purpose of knee skyline photographing, the presence of the patient is detected by the proximity sensor 122 of the cassette sensor 104.

Thus the sensor to be used for photographing can be automatically recognized.

Also, in case of photographing the head of the patient by the cassette sensor 104 while the patient lies on the examination table 103, both proximity sensors 121, 122 of the examination table 103 and the cassette sensor 104 are activated. In such case (when the examination table sensor 103 and the cassette sensor 104 are in competition), the priority is given to the cassette sensor 104 and the system recognizes the photographing by the cassette sensor 104.

For example when the X-ray is generated from the X-ray generation device 101 while the patient stands in front of the standing position stand sensor 102 to activate the proximity sensor 120 thereof, a radiation image of the patient obtained by the standing position stand sensor 102 is fetched into the computer 105.

In the computer 105, the data collection unit 107 collects the radiation image from the standing position stand sensor 102.

The image processing unit 108 executes judgment and learning of the photographing position (position of the object at photographing and photographing method) on the radiation image collected by the data collection unit 107, then determines the image processing parameters according to the result of judgment of the photographing position, and executes image processing utilizing such image processing parameters. The configuration and function of the image processing unit 108, to be explained later, are most significant features of the present invention.

The data transfer unit 109 transfers the radiation image after the processing in the image processing unit 108, as a QA (quality assurance) image, to the data storage device 112 and/or the printer 113.

The data storage device 112 stores the QA image from the data transfer unit 109, while the printer 113 prints the radiation image from the data transfer unit 109 in response to an instruction for example from the radiologist.

The QA image stored in the data storage device 112 or printed by the printer 113 as explained above is used for example for diagnosis by doctors.

Details of the Image Processing Unit 108 of the Computer 105

The image processing unit 108, having a configuration constituting the most significant feature of the present embodiment, is provided for example with a pre-processing unit 200, a reduced image generating unit 201, an irradiation field restriction presence/absence judgment unit 202, an irradiation field extraction unit 203, a direct irradiation area extraction unit 204, a characteristic amount extraction unit 205, a photographing position/photographing method judgment unit 206, a photographing position determination unit 207, an image processing parameter determination unit 208, a dynamic range compression unit 209, a frequency enhancement unit 210, a gradation conversion unit 211 and a storage device 220, as shown in FIG. 3.

In the above-described image processing unit 108, the pre-processing unit 200 at first applies pre-processing such as offset correction, logarithmic conversion, gain correction etc. on the radiation image (hereinafter simply called "image") from the data collection unit 107, and sends thus processed image as an original image to the storage unit 220 and the reduced image generating unit 201.

The storage unit 220 stores the original image from the pre-processing unit 200 in a memory medium (for example a magnetic disk) set in the storage unit 220.

On the other hand, the reduced image generating unit 201 generates a reduced image from the original image supplied from the pre-processing unit 200.

The size of the original image depends on the sensor selected from the standing position stand sensor 102, the examination table sensor 103 and the cassette sensor 104.

In the present embodiment, the standing position stand sensor 102 and the examination table sensor 103 are assumed to have a size of 2688×2688 pixels while the cassette sensor 104 is assumed to have a size of 1840×2320 pixels.

Also the reduced image generating unit 201 compresses the size of the original image by skipping each side thereof to 1/16.

Consequently, in case of photographing with the standing position stand sensor 102, the original image after processing in the reduced image generating unit 201 has a size of 168×168 pixels. In such processing, the average value of 16×16 pixels may be employed as the pixel value of the reduced image.

The reduced image obtained in the reduced image generating unit 201 is supplied to the irradiation field restriction presence/absence judgment unit 202 and the irradiation field extraction unit 203.

The irradiation field restriction presence/absence judgment unit 202 applies the following field restriction presence/absence judging process on the reduced image from the reduced image generating unit 201.

The irradiation field restriction presence/absence judging process judges, in photographing the object, whether the X-ray irradiation field is restricted or left open. The result of judgment (irradiation field restriction presence/absence information) is used as a characteristic amount for judging the photographing position (photographing method) as will be explained later.

In the present embodiment, the presence or absence of the irradiation field restriction is judged for example by a method disclosed in the Japanese Patent Application Laid-open No. 11-089823. The method searches, in the object image, an area containing pixels of which values are close to a pixel value sampled from the peripheral portion of the sensor, and utilizes the frequency of generation of such close values.

The judgment of presence or absence of the irradiation field restriction is not limited to the above-mentioned method but can also be achieved, for example, by generating a histogram of the object image and evaluating such histogram with a threshold value.

The result of judgment of the irradiation field restriction presence/absence judging unit 202 is supplied to the irradiation field extraction unit 203.

In case the result of judgment by the irradiation field restriction presence/absence judging unit 202 indicates that an irradiation field is present in the object image (reduced image obtained in the reduced image generating unit 201), the irradiation field extraction unit 203 extracts the irradiation field from such reduced image.

In the present embodiment, the irradiation field is extracted for example by a method disclosed in the Japanese Patent Application Laid-open No. 10-243456. This method consists of taking profiles of the object image at a constant interval and taking a train of points of highest boundary estimated from the profiles as the boundary.

Consequently, in case the irradiation field restriction is present in the object image, the direct irradiation area extraction unit 204 is given an image of an even smaller size corresponding to the irradiation field image cut out from the reduced image of 168×168 pixels. Also in case the irradiation field restriction is absent in the object image, the entire reduced image of 168×168 pixels is given as the irradiation field image.

The direct irradiation area extraction unit 204 specifies, based on the histogram of the irradiation field image supplied from the irradiation field extraction unit 203, an area of a high X-ray dose and recognizes the connection state of such area with the peripheral area, thereby determining a direct irradiation area (subjected to direction X-ray irradiation) in the irradiation field image. In this operation there is taken into consideration that the direct irradiation area is present in the peripheral area of the irradiation field.

The direct irradiation area obtained by the direction irradiation are extraction unit 204 is supplied, together with the corresponding irradiation field image, to the characteristic amount extraction unit 205.

The characteristic amount extraction unit 205 extracts plural characteristic amounts from the reduced image, based on the irradiation field image and its direct irradiation area supplied from the direction irradiation area extraction unit 204, as will be explained later in more details, and supplies the photographing position judgment unit 206 with such characteristic amounts.

Figure 4:
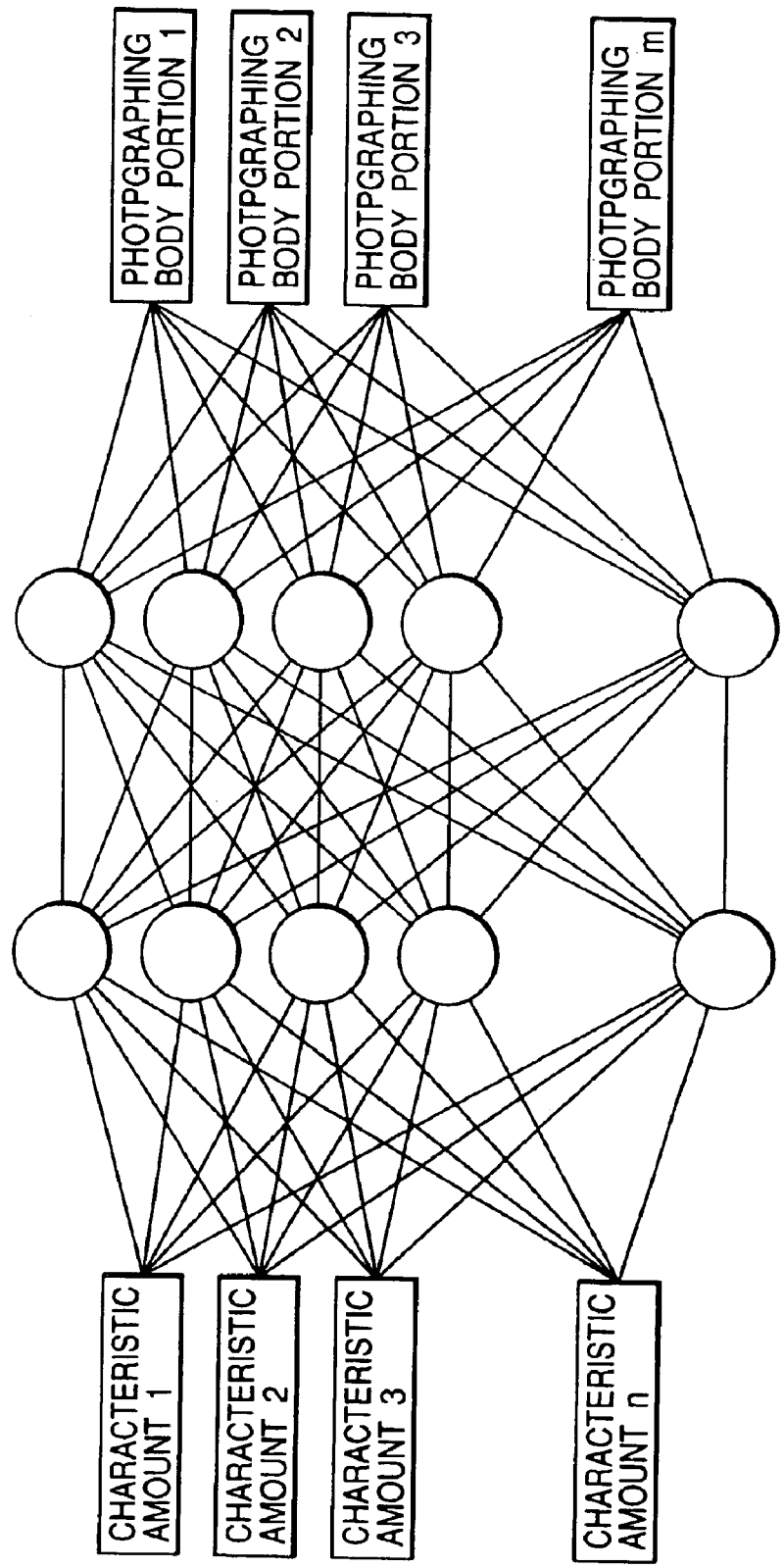
FIG. 4 is a view showing the judgment and learning of the photographing position in the above-mentioned image processing unit.

The photographing position judgment unit 206 judges the photographing position (photographing method) of the object image (reduced image), based on the characteristic amounts supplied from the characteristic amount extraction unit 205. In this operation, there is utilized a neural network as shown in FIG. 4.

More specifically, for the algorithm relating to learning and testing of the neural network, there can be utilized, for example, the inverse error propagation method developed by Rumelhart et al., as described by Hideki Takahashi in Neural Network Information Processing, 2.1.4.

The characteristic amounts are basically entered directly into the neural network, but, for a characteristic amount having binary result such as the presence or absence of the irradiation field restriction, values "1" and "0" are assigned to such characteristic amount, such as "1" for presence and "0" for absence of the irradiation field restriction.

Also the result of the neural network is outputted in the following manner. For example, in case the photographing positions 1 and 2 respectively correspond to a chest front image and a chest lateral image, the output of the photographing position 1 assumes a value "1" while the outputs of other photographing positions 2, 3, . . . assumes a value "0" for an object image consisting of a chest front image. Also for a chest lateral image, the output of the photographing position 2 assumes a value "1" while those of other photographing positions 1, 3, . . . assume a value "0".

In case the result of judgment of the photographing position is not clear at the output of the result of the neural network, a most probable result is selected. As the result of the neural network increases for a higher probability, there is selected a photographing position showing the highest output value.

The above-described result of judgment in the photographing position judging unit 206 is supplied once to the console 106 (cf. FIG. 1).

Figure 2C:
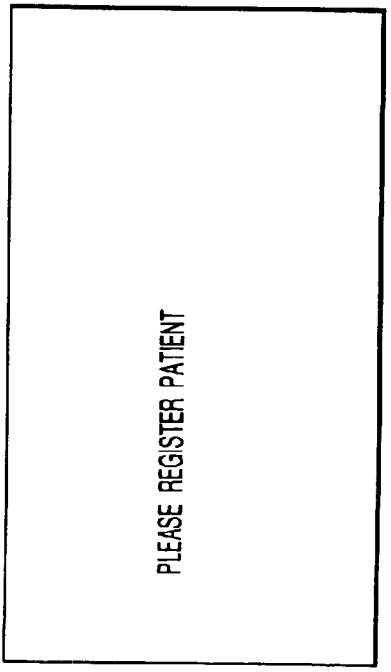

Thus, if the result of judgment in the photographing position judging unit 206 indicates a "chest front image", the console 106 displays an image, as shown in FIG. 2C, after the first photographing. More specifically, with the execution of X-ray irradiation, the display shifts from the image indicating that the photographing operation is possible as shown in FIG. 2B to the image indicating the information on the photographing position as shown in FIG. 2C.

The image shown in FIG. 2C indicates, together with the reduced image of the photographed image (namely "image 1" obtained by the first photographing), a message indicating the result of judgment of the photographing position (photographing position of the image 1), such as "frontal chest image". The image also includes operation buttons such as "body position correction" for correcting the judged photographing position and "image adjustment".

The result of judgment of the photographing position judging unit 206 (photographing position judgment result) and the characteristic amounts used for such judgment (obtained by the characteristic amount extraction unit 205) are stored in an internal memory (not shown) of the computer 105.

The computer 105 calculates the rate of correctness of the photographing position judgment results stored in such internal memory, and, if such rate of correctness is lower than a predetermined reference rate, instructs the console 6 to display an image indicating the execution of learning operation in the photographing method judgment unit 206 and causes the photographing position judgment unit 206 to initiate the learning process. In this learning process, there are utilized the photographing position judgment result and the characteristic amounts stored in the aforementioned internal memory.

Then the operator confirms the image shown in FIG. 2C, displayed on the console 106, and, if the actual photographing position of the patient coincides with the photographing position judged in the photographing system 100 (namely the result of judgment by the photographing position judging unit 206), depresses the irradiation button (not shown) for the next (second) photographing. The execution of this irradiation means that the judgment of the photographing position judging unit 206 is approved by the operator.

On the other hand, if the actual photographing position of the patient does not coincide with the photographing position judged in the photographing system 100 (namely the result of judgment by the photographing position judging unit 206), the operator depresses the "body position correction" button 2010 displayed on the console 106 (cf. FIG. 2C).

Figure 2D:
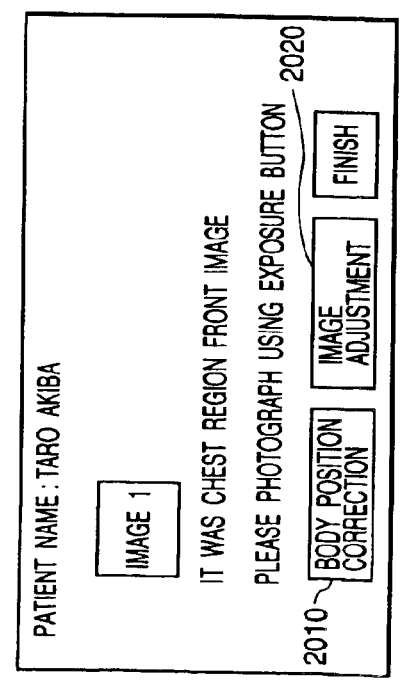

More specifically, at the completion of the second photographing, the console 106 displays an image as shown in FIG. 2D.

Then the operator confirms the image shown in FIG. 2D, and, if the second photographed image is judged by the photographing position judging unit 206 as a thoracic vertebrae lateral image but the actual photographing position of the patient is a chest lateral photographing, depresses the "body position correction" button 2010 displayed on the console 106.

Figure 5:
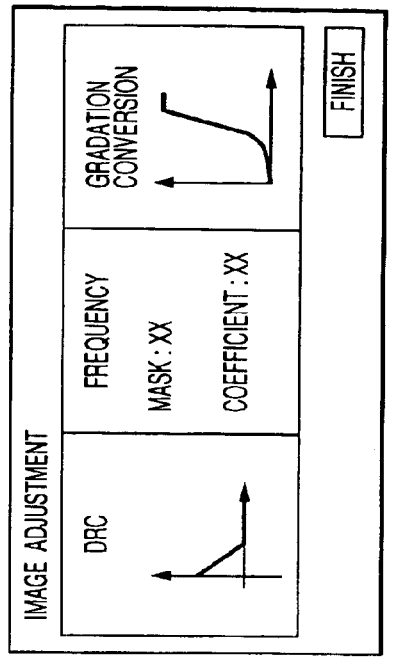
FIGS. 5A, 5B, 5C and 5D are views showing display images for correcting the photographing position and for adjusting the image, to be displayed on the above-mentioned console.

The information of such button depression is supplied to the computer 105, which in response displays an image for correction on the console 106, as shown in FIG. 5A.

Then the operator depresses, among the buttons indicating various photographing position in the correcting image shown in FIG. 5A, a button corresponding to the correct photographing position ("chest front" in the present case). Such correction of the photographing position is reflected on the image shown in FIG. 2D.

Then the operator depresses the irradiation button (not shown) for the next (third) photographing. The execution of this irradiation means that the judgment of the photographing position judging unit 206 is approved by the operator.

The photographing position determination unit 207 determines the photographing position, based on the "approval" by the aforementioned depression of the irradiation button.

The process of the photographing position determination unit 207 is executed for each photographing operation (first photographing, second photographing, . . . ). Also each of the processes to be explained in the following is executed for each photographing operation, based on the photographing position determined for each photographing by the photographing position determination unit 207.

The image processing parameter determination unit 208 determines the image processing parameters for the object image, by referring to a predetermined image processing parameter table, based on the photographing position determined by the photographing position determination unit 207.

More specifically, the image processing parameter table is stored in advance in a magnetic disk of the storage unit 220. The image processing parameter determination unit 208 downloads the image processing parameter table from the storage unit 220 based on the determination of the photographing position by the photographing position determination unit 207, and searches and determines the image processing parameters for the object image from such parameter table.

FIG. 6 shows an example of the image processing parameter table. As shown in FIG. 6, the image processing parameter table contains HD curve, gamma value, central density, frequency enhancement pattern and DRC pattern corresponding to various photographing positions.

Thus, if the photographing position of the object image determined by the photographing method determination unit 207 for example corresponds to chest front photographing, the image parameter determination unit 208 determines a set of the image processing parameters corresponding to the chest front photographing in the parameter table, namely an HD curve "1", a gamma "2.88", a central density "1.4", a frequency enhancement pattern "1" and a DRC pattern "2", for the object image.

It is also possible to set the image processing parameter table, as shown in FIG. 6, in the storage unit 220 in such a manner as desired by the user, for each hospital in which the photographing system 100 is installed.

The dynamic range compression unit (DRC) 209 reads the original image of the object image stored in the magnetic disk of the storage unit 220, and executes a dynamic range compression process on such original image, based on the image processing parameters determined by the image processing parameter determination unit 208.

The frequency enhancement unit 210 applies a frequency enhancement process on the image after processing by the dynamic range compression unit 209, based on the image processing parameters determined by the image processing parameter determination unit 208.

The gradation conversion unit 211 executes a gradation conversion process on the image after processing by the frequency enhancement unit 210 based on the image processing parameters determined by the image processing parameter determination unit 208.

The image after processing by the gradation conversion unit 211 constitutes the output of the image processing unit 108, and is supplied as a QA (quality assurance) image to the data transfer unit 109.

The data transfer unit 109 transfers the QA image from the image processing unit 108 to at least either of the data storage device 112 and the printer 113.

However the QA image obtained as explained in the foregoing may not be the image desired by the operator. More specifically, for certain objects, the desired QA image may not be obtained from the currently stored standard image processing parameter table (cf. FIG. 6). In such case, the operator (radiologist or doctor) can manually execute fine adjustment of the image processing parameters.

For example, if the operator observes the image 1 or 2 displayed as shown in FIG. 2C or 2D and finds that such image is not in the desired state, the operator depresses the "image adjustment" button 2020 shown in the displayed image.

In response, the console 106 displays an image shown in FIG. 5B, in which the image processing parameters (those used for DRC, frequency enhancement and gradation conversion) can be finely adjusted.

Thus the operator executes fine adjustment of the image processing parameters on the image shown in FIG. 5B. The result of such adjustment is fed back to the image processing parameter determination unit 208, which thereafter executes the process with thus adjusted image processing parameters.
Details of the Characteristic Amount Extraction Unit 205 of the Image Processing Unit 108

Figure 7:
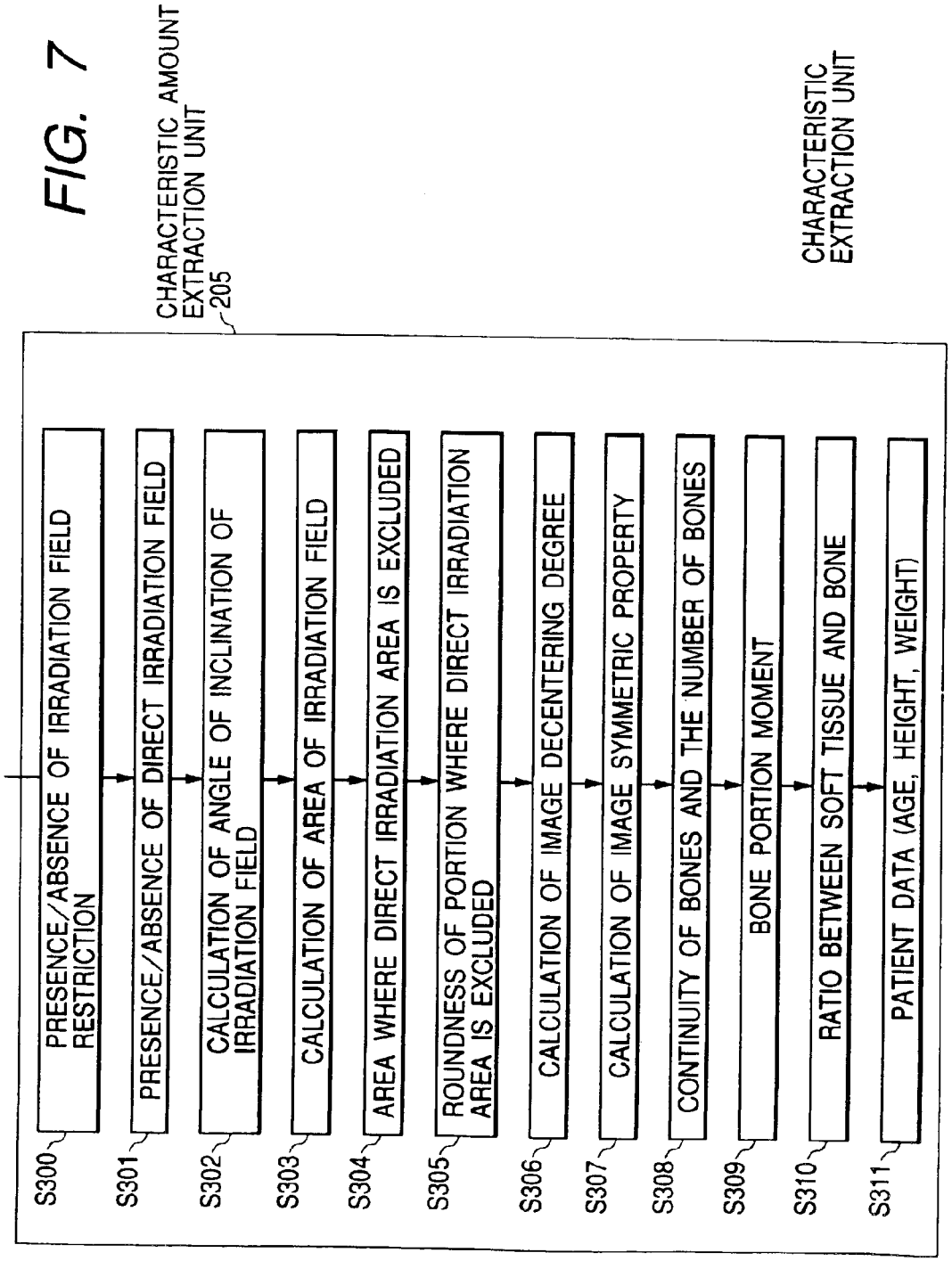
FIG. 7 is a view showing the processing of a characteristic amount extraction unit of the above-mentioned image processing unit.

The characteristic amount extraction unit 205 in the image processing unit 108 extracts the plural characteristic amounts to be used in determining the image processing parameters for the reduced (object) image based on the reduced image and the direct irradiation area thereof from the direction irradiation area extraction unit 204, for example by executing steps S300 to S311 shown in FIG. 7.

At first there is specified whether the irradiation field restriction is present in the reduced image corresponding to the irradiation field image supplied from the direct irradiation area extraction unit 204 (step S300).

Such operation can be achieved by adopting the result of judgment by the irradiation field restriction presence/absence judging unit 202.

Then there is specified whether the direct irradiation area is present or absent in the object image (step S301). Such operation can be achieved by adopting the result of extraction by the direct irradiation area extraction unit 204.

Then there is calculated the inclination angle of the irradiation field area of the object image, obtained in the step S300 (step S302).

Figure 8:
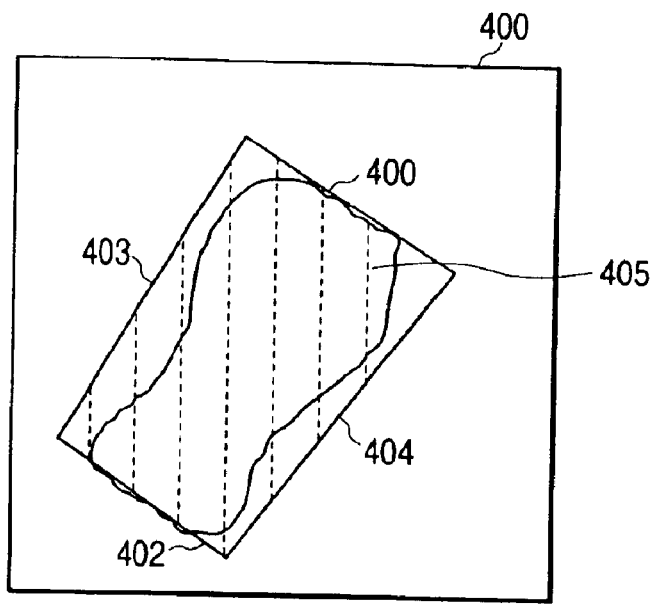
FIG. 8 is a view showing the extraction of a characteristic amount (inclination angle of irradiation field) in the above-mentioned characteristic amount extraction unit.

For example, if the object image consists of an image 400 of an elbow area 405 as shown in FIG. 8, a rectangular area (hatched area consisting of sides 401 to 404) surrounding the elbow area 405 is cut out from the image 400 (entire sensor area), and the inclination angle θ of the irradiation field area is calculated from the angles θ1 to θ4 of the sides 401 to 404 according to the following equation:

$$\theta=0.5\times|\theta1+\theta2-\theta3-\theta4|$$

If the inclination angle θ is not about 90°, the object image is often of extremities and exceptionally of cervical vertebrae.

Then there is calculated the area of the irradiation field area obtained in the step S302 (hatched rectangular area shown in FIG. 8) (step S303).

The area of the rectangular area shown in FIG. 8 is calculated for example by dividing the rectangular area into triangles and adding the areas of such triangles.

Then there is calculated the remaining area after deduction of the direct irradiation area obtained in the step S301 from the object area (step S304).

Figure 9:
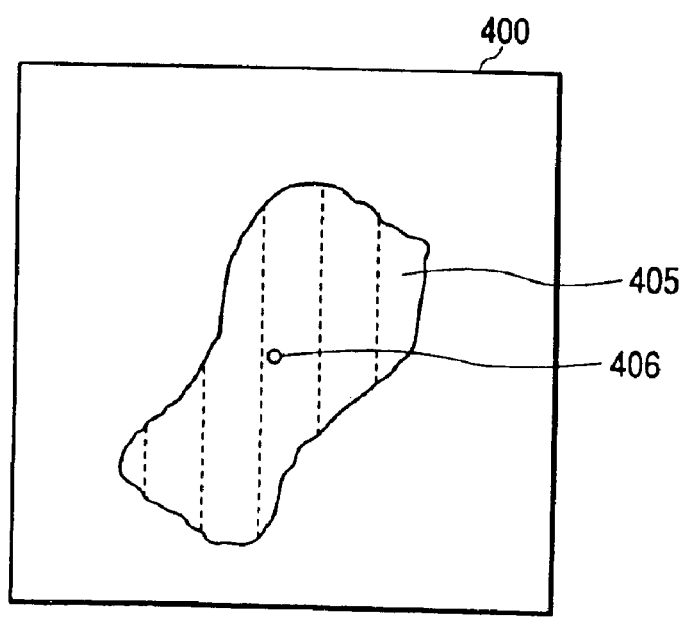
FIG. 9 is a view showing the extraction of a characteristic amount (roundness of a portion excluding direct irradiation area) in the above-mentioned characteristic amount extraction unit.

For example, in case the object image consists of the image 400 of the elbow area 405 as shown in FIG. 8, the hatched area or the elbow area 405 as shown in FIG. 9 can be obtained by deducting the direction irradiation area from the image 400. The remaining area (elbow area 405) after the deduction of the direct irradiation area from the object image can be determined by calculating the number of pixels in such elbow area 405. The area thus obtained can be used as a characteristic amount in combination with the patient information (age, weight, height etc.) to be explained later, whereby effective image processing parameters can be obtained.

Then there is calculated roundness of the area obtained in the step S304 by deducting the direction irradiation area from the object image (step S305).

For example, in case the area after deduction of the direct irradiation area from the object image is the elbow area 405 shown in FIG. 9, the circumferential length T and area S of the elbow area 405 are measured and the roundness is calculated by:

$$\text{roundness}=T2/4\pi S$$

In the foregoing equation, the circumferential length T is calculated from boundary lines X(t), Y(t) represented by the coordinate of the center 406 of gravity of the elbow area 405, according to the following equation:

$$T=\int \sqrt{(X2(t)+Y2(t))}dt.$$

Such roundness constitutes an important characteristic amount in case the object image is a head image, and becomes a characteristic index in case of forming the boundary of the irradiation field restriction inside the body as in a thoracic front or lateral image.

The calculation method for roundness in the step S305 is described in detail for example by Anil K. Jain, "Fundamentals of Digital Image Processing", Prentice Hall, pp391, 1989.

Then the eccentricity of the object image is calculated from the center of gravity of the area after deduction of the direct irradiation area from the object image (center 406 of gravity of the elbow area 405 in case of FIG. 9) (step S306).

For example, in case of FIG. 9, the center 406 of gravity of the elbow area 405 can be obtained by averaging the coordinates of the pixel points of the elbow area (hatched area) 405. Also the eccentricity is equivalent to moment. Therefore, the eccentricity can be determined by calculating the moment of the image area, after deduction of the direct irradiation area, about the center 406 of gravity.

The calculation of the center of gravity and the moment in the step S305 is also described in detail for example by Anil K. Jain, "Fundamentals of Digital Image Processing", Prentice Hall, pp391, 1989.

Then there is calculated, for the area after deduction of the direct irradiation area from the object image, the symmetry with respect to a line passing through the center of gravity of such area and having an inclination angel θ of the irradiation field area (hereinafter called "object line") (step S307).

Figure 10:
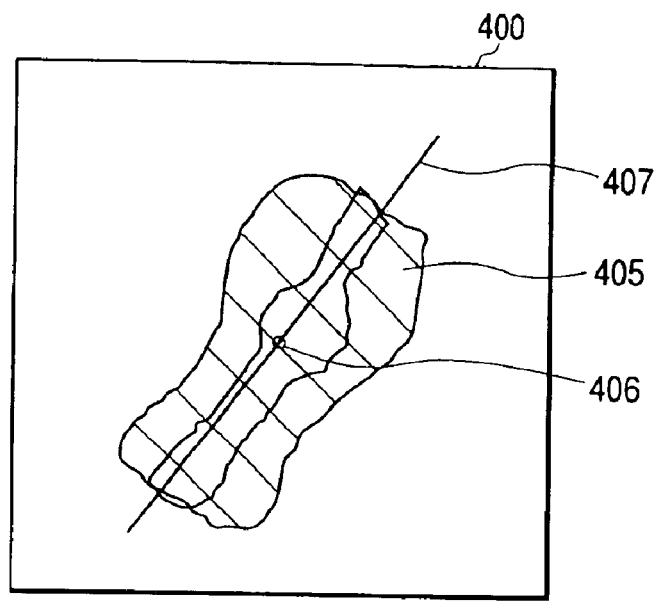
FIG. 10 is a view showing the extraction of a characteristic amount (symmetry of image) in the above-mentioned characteristic amount extraction unit.

For example, in case the area after deduction of the direct irradiation area from the object image consists of the elbow area 405 shown in FIG. 9, there is calculated the symmetry Sy with respect to an object line passing through the center 406 of gravity of the elbow area 405 as shown in FIG. 10. In this calculation, the elbow area 405 is regarded as a group of dots and as the original multi-value image instead of a binary image.

The symmetry Sy is calculated from left and right images L(t), R(t) obtained by dividing the object image with the object line, according to the following equation:

$$Sy=\Sigma|L(t)-R(t)|$$

The area (body area) after deduction of the direct irradiation area from the object image becomes more symmetrical as the symmetry value Sy decreases. In general, a front image shows higher level of symmetry.

Then, in the area (body portion) after deduction of the direct irradiation area from the object image, a portion of bones is extracted by deleting a soft tissue portion by binarization, and the number of bones is calculated from the continuity of such bone portion (step S308). In this operation, the threshold value of binarization can be determined by separation from the histogram, and the number of bones can be determined by a labeling process.

Figure 11:
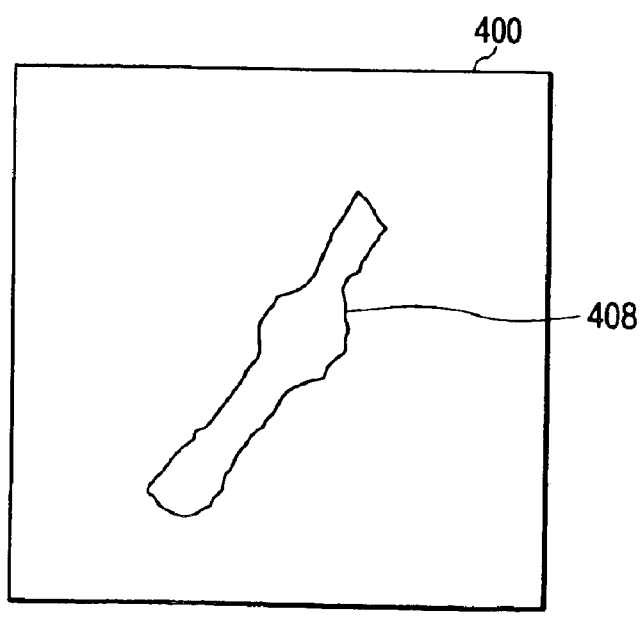
FIG. 11 is a view showing the extraction of a characteristic amount (continuity and number of bones) in the above-mentioned characteristic amount extraction unit.

Consequently, in case the area after deduction of the direct irradiation area from the object image is the elbow area 405 as shown in FIG. 9 or FIG. 10, there can be calculated number (one) of the bone portion 408 as shown in FIG. 11.

Then there is calculated the moment of the bone portion obtained in the step S308 (step S309).

For example, the center of gravity of the bone portion is determined on the binary image as in the calculation of eccentricity in the step S306, and the moment of the bone portion is calculated on the multi-value image about thus determined center of gravity. In case of an image of extremities, the moment becomes small for a hand or a medium leg portion but large for an upper arm or a thigh.

Then there is calculated, in the area after deduction of the direct irradiation area from the object image, the ratio of the soft tissue portion and the bone portion (step S310). For example the area ratio of these portions is determined on the binary image.

The ratio thus obtained depends significantly on the accuracy of binarization in determining the continuity and number of bones in the step S308, but the proportion of bones is generally large in case the object image is a head image or an abdominal image and small in case the object image is a chest image, because of the influence of the lung area.

Finally, the patient information is acquired as the most important characteristic amount (step S311).

The patient information (age, height, weight etc.) is not obtained by calculation but from the input by the operator on the character input unit 111 (cf. FIG. 1) or from the hospital card of the patient, read by the magnetic card reader 110.

The patient information obtained in the step S311 is added as characteristic amounts because the characteristic amount, for example constituted by the area after deduction of the direct irradiation area from the object image such as a chest front image, is not accurate enough as the object area significantly differs between a child and an adult. The probability of photographing the image of a child is generally low except in a pediatric hospital, but the use of the age significantly improves the accuracy of the characteristic amounts of the image obtained by photographing a child.

In the present embodiment, there are determined the inclination angle of the irradiation field, area of the irradiation field, area after deduction of the direct irradiation area, roundness of the area after deduction of the direction irradiation area, eccentricity of the image, symmetry of the image, continuity of the bones, number of the bones, ratio of the soft tissue portion and the bone portion and patient information (age, height, weight etc.) as the characteristic amounts of the object image, but such example of the characteristic amounts is not restrictive.

Second Embodiment

In the foregoing first embodiment, the photographing of the patient is initiated in response to the insertion of the hospital card, carried by the patient, into the magnetic card reader 110 or the input of the patient information by the operator through the character input unit 111. In the present second embodiment, the photographing of the patient is initiated by a patient selection image displayed on the console 106, as shown in FIG. 12A.

More specifically, the computer 105 at first acquires a list of the patients from a hospital information system (HIS) or a radiology information system (RIS), and causes the console 106 to display such patient list.

Thus the console 106 displays an image shown in FIG. 12A.

Then the operator selects the patient to be photographed, utilizing the instruction means (not shown) of the console 106, on the image (cf. FIG. 12A) displayed thereon.

Upon recognizing the selecting operation on the console 106, the computer 105 shifts the display of the console 106 to a state shown in FIG. 12B.

The image shown in FIG. 12B displays, together with the patient selected in the image of FIG. 12A, a message indicating that the photographing is possible (for example "Depress the irradiation button for photographing"). The image in FIG. 12B indicates selection of a patient Haruna and the computer 105 is assumed to recognize that the photographing of front and lateral images of the thoracic vertebrae has been requested from the network for the patient Haruna.

The photographing of the patient is initiated in the same manner as in the first embodiment, in response to the display of the image shown in FIG. 12B on the console 106 and to the depression of the irradiation button (not shown) by the operator.

If two photographing positions, for example front and lateral positions of the thoracic vertebrae, are selected in the judgment of the photographing position, a position showing a larger output of the neural network is selected as the current photographing position of the object image, as already explained in the foregoing.

Thus the console 106 displays, as shown in FIG. 12C, the information of thus determined photographing position (message "thoracic vertebrae front image"), together with the object image (image 1).

The operator confirms the image shown in FIG. 12C, and, if the result of judgment of the photographing position displayed on such image is correct, depresses the irradiation button for a next (second) photographing, whereupon the next photographing is initiated.

On the other hand, if the result of judgment of the photographing position is incorrect, the operator depressed the "body position correction" button 2010 shown in FIG. 12C.

In response, the console 106 displays an image as shown in FIG. 5C.

In the foregoing first embodiment, in response to the depression of the "body position correction" button 2010, there is displays an image shown in FIG. 5A. In contrast, in the present embodiment, there is displayed an image shown in FIG. 5C, which displays the photographing methods (front and lateral) contained in the photographing list only, namely the photographing position (thoracic vertebrae in this case) only recognized by the computer 105 prior to the start of photographing.

In response the operator selects and depresses a button corresponding to the proper photographing position among those displayed in the image shown in FIG. 5C. Such correction of the photographing position is reflected on the image shown in FIG. 12C.

The operator initiates the next (second) photographing by depressing the irradiation button (not shown).

After the two photographing operations as explained in the foregoing, the console 106 displays an image shown in FIG. 12D.

As shown in FIG. 12D, there are displayed images 1 and 2 obtained by the two photographings. In this state, it is assumed that two photographings have been requested, of which the first one is already completed. Therefore, if the output of the neural network is ambiguous for the second photographing, it probably indicates the remaining photographing and such remaining photographing is preferentially outputted as the result of judgment.

Third Embodiment

The present embodiment limits the range of the result of judgment of the photographing position in the foregoing first embodiment, based on the information of the sensor employed for photographing.

At first the console 106 displays an image as shown in FIG. 2A for registering the patient, whereby the patient is set on the standing position stand sensor 102, the examination table sensor 103 or the cassette sensor 104.

As an example, it is assumed that a certain body portion of the patient is set on the cassette sensor 104.

In the internal memory (not shown) of the computer 105, there is defined in advance the photographing position of the patient to be photographed by the cassette sensor 104, according to the principle of the hospital in which the photographing system 100 is installed.

Thus, in judging the photographing position based on the output of the neural network, it is rendered possible to limit the judgment within a range of the photographing positions set in the internal memory of the computer 105, thereby improving the probability of correct judgment of the photographing position.

The photographing position by the cassette sensor 104 includes, for example, shoulder front, shoulder axial, elbow front, elbow lateral, hand front and hand lateral.

Therefore the photographing positions on the cassette sensor 104 are limited to such six positions. In such case, if the result of judgment of the photographing position based on the output of the neural network is erroneous and the "body position correction" button is depressed by the operator, the console 106 displays an image as shown in FIG. 5D, in which the candidates for correction are also limited.

Fourth Embodiment

In the foregoing first embodiment, the photographing of the patient is initiated in response to the insertion of the hospital card, carried by the patient, into the magnetic card reader 110 or the input of the patient information by the operator through the character input unit 111. In the present embodiment, the photographing of the patient is initiated by a patient selection image displayed on the console 106, as shown in FIG. 13A.

More specifically, the computer 105 at first acquires a list of the patients from a hospital information system (HIS) or a radiology information system (RIS), and causes the console 106 to display such patient list.

Thus the console 106 displays an image shown in FIG. 13A.

Then the operator selects the patient to be photographed, utilizing the instruction means (not shown) of the console 106, on the image (cf. FIG. 13A) displayed thereon.

Upon recognizing the selecting operation on the console 106, the computer 105 shifts the display of the console 106 to a state shown in FIG. 13B.

The image shown in FIG. 13B displays, together with the patient selected in the image of FIG. 12A, a message indicating that the photographing is possible (for example "Depress the irradiation button for photographing"). The start of the photographing operation is enabled after the photographing position of the patient is selected.

The image in FIG. 13B indicates selection of a patient Haruna and, as the photographing position for the patient Haruna, there can be selected either "thoracic vertebrae front" or "thoracic vertebrae lateral".

Thus the operator selects either "thoracic vertebrae front" or "thoracic vertebrae lateral" on the image shown in FIG. 13B (selection of "thoracic vertebrae front" being indicated by a black square) and then depresses the irradiation button (not shown). The front photographing of the thoracic vertebrae of the patient is thus initiated in the same manner as in the first embodiment.

It is also possible for the operator to execute the photographing operations in the positions such as "thoracic vertebrae front" and "thoracic vertebrae lateral" in succession according to the order designated from the RIS, or to alter the order of photographings by the designation means (not shown) of the console 106, on the image displayed thereon.

If two photographing positions, for example front and lateral positions of the thoracic vertebrae, are selected in the judgment of the photographing position, the output of the neural network is limited to such two photographing positions and a position showing a larger output is selected as the current photographing position of the object image.

Thus the console 106 displays, as shown in FIG. 13C, the information of thus determined photographing position (message "thoracic vertebrae lateral image"), together with the object image (image 1). Also the console 106 displays a position yet to be photographed and a black square indicating the selection of the predetermined position.

The operator confirms the image shown in FIG. 13C, and, if the result of judgment of the photographing position displayed on such image is correct, depresses the irradiation button for a next (second) photographing, whereupon the next photographing is initiated.

On the other hand, if the result of judgment of the photographing position is incorrect, the operator depressed the "body position correction" button 2010 shown in FIG. 13C.

In response, the console 106 displays an image as shown in FIG. 5C.

In the foregoing first embodiment, in response to the depression of the "body position correction" button 2010, there is displays an image shown in FIG. 5A. In contrast, in the present embodiment, there is displayed an image shown in FIG. 5C, which displays the photographing methods contained in the photographing list only, namely the photographing position (thoracic vertebrae in this case) only recognized by the computer 105 prior to the start of photographing.

In response the operator selects and depresses a button corresponding to the proper photographing position among those displayed in the image shown in FIG. 5C. Such correction of the photographing position is reflected on the image shown in FIG. 13C. The correction is also reflected in the display of the position yet to be photographed and the black square (cf. FIG. 13C).

The operator initiates the next (second) photographing by depressing the irradiation button (not shown).

In the foregoing there has been explained a case where, if the position selected prior to the photographing is different from that judged after the photographing, the position is immediately replaced by the latter, but it is also possible to provide a warning display indicating such difference in the position and to cause the operator to select the former or the latter.

After the two photographing operations as explained in the foregoing, the console 106 displays an image shown in FIG. 13D.

As shown in FIG. 13D, there are displayed images 1 and 2 obtained by the two photographings. In this state, it is assumed that two photographings have been requested, of which the first one is already completed, so that the next photographing is probably the remaining photographing. However, the next photographing may still be executed erroneously, but the photographing system 100 of the present embodiment can prevent failure in the photographing operation, because there is provided a checking function including the display of the photographing position yet to be photographed and the judgment of the photographing position.

The objects of the present invention can naturally be attained also in a case where a memory medium storing the program codes of a software realizing the functions of the aforementioned first to fourth embodiments is supplied to a system or an apparatus and the functions of the aforementioned embodiments are realized by a computer (CPU or MPU) of the above-mentioned system or apparatus by reading and executing the program codes stored in the memory medium.

In such case the program codes themselves of the software realize the novel functions of the present invention, and the memory medium storing the program codes constitutes the present invention.

The memory medium storing such program codes can be, for example, a ROM, a floppy disk, a hard disk, an optical disk, a magnetooptical disk, a CD-ROM, a CD-R, a magnetic tape or a non-volatile memory card.

The present invention also includes not only a case where the functions of the aforementioned embodiments are realized by the execution of the program codes read by the computer but also a case where an operating system or the like functioning on the computer executes all or a part of the actual processes under the control of such program codes thereby realizing the functions of the foregoing embodiments.

The present invention further includes a case wherein the program codes read from the memory medium are once stored in a function expansion board inserted into the computer or a function expansion unit connected to the computer, and a CPU provided in the function expansion board or the function expansion unit executes all the process or a part thereof under the control of such program codes, thereby realizing the functions of the aforementioned embodiments.

The present invention is not limited to the foregoing embodiments but is subject to various modifications within the spirit and scope of the appended claims.

What is claimed is:

1. An apparatus for processing an image of an object, comprising:
   radiation generation means for generating X-rays;
   a two-dimensional X-ray sensor for obtaining X-rays generated by said radiation generation means and transmitted through the object, as an image;
   calculation means for calculating, from the image obtained by said two-dimensional X-ray sensor, a feature amount to be used to discriminate which of plural categories the object belongs to;
   first input means for inputting the plural categories corresponding to the object;
   discrimination means for discriminating the category of the object based on the feature amount calculated by said calculation means;
   second input means for inputting a correction signal or an approval signal, corresponding to the category of the object; and
   determination means for determining the category of the object based on the category discriminated by said discrimination means and the signal input using said second input means,
   wherein, when the plural categories are input by said first input means, said discrimination means discriminates the category of the object from among the plural categories, and
   wherein said determination means determines, as the category of the object, the category discriminated by said discrimination means when the approval signal is input, and determines, as the category of the object, the category corresponding to the correction signal when the correction signal is input.

2. An apparatus according to claim 1, further comprising:
   storage means for storing an image processing parameter corresponding to the category of the object; and
   image processing means for performing an image process on the image by calling out the image processing parameter from said storage means on the basis of the category determined by said determination means.

3. An apparatus according to claim 2, further comprising display means for displaying the discrimination result obtained by said discrimination means.

4. An apparatus according to claim 2, further comprising:
   information storage means for storing the feature amount and the category determined by said determination means; and
   learning means for changing a discrimination algorithm to be used by said discrimination means based on the information stored by said information storage means.

5. An apparatus according to claim 2, wherein the image process to be performed by said image processing means is one or more selected from: a gradation conversion process, a frequency emphasis process and a dynamic range compression process.

6. An apparatus according to claim 1, further comprising display means for displaying the discrimination result obtained by said discrimination means.

7. An apparatus according to claim 1, further comprising information input means for inputting information concerning the object,
   wherein said discrimination means discriminates the category of the object based on the input information concerning the object and the feature amount.

8. An apparatus according to claim 1, further comprising:
   information storage means for storing the feature amount and the category determined by said determination means; and
   learning means for changing a discrimination algorithm to be used by said discrimination means based on the information stored by said information storage means.

9. An apparatus for processing an image of an object, comprising:
   radiation generation means for generating X-rays;
   plural kinds of two-dimensional X-ray sensors for obtaining the X-rays generated by said radiation generation means and transmitted through the object, as an image;
   selection means for selecting one of said plural kinds of two-dimensional X-ray sensors;
   calculation means for calculating, from the image obtained by said two-dimensional X-ray sensor selected by said selection means, a feature amount to be used to discriminate a category, among plural categories, to which the object belongs;
   input means for inputting the plural categories corresponding to the object; and
   discrimination means for discriminating the category of the object based on the feature amount calculated by said calculation means,
   wherein, when the plural categories are input by said input means, said discrimination means discriminates the category of the object from among the plural categories, and
   wherein said discrimination means changes a discrimination rule based on the kind of two-dimensional X-ray sensor selected by said selection means.

10. A method of processing an image of an object, comprising:
    a radiation generation step of generating X-rays;
    a two-dimensional X-ray sensing step, of obtaining the X-rays generated in said radiation generation step and transmitted through the object, as an image;

a calculation step of calculating, from the image obtained in said two-dimensional X-ray sensing step, a feature amount to be used to discriminate a category, form among plural categories, to which the object belongs;

a first input step of inputting the plural categories corresponding to the object;

a discrimination step of discriminating the category of the object based on the feature amount calculated in said calculation step;

a second input step of inputting a correction signal or an approval signal, corresponding to the category of the object; and a determination step of determining the category of the object based on the category discriminated in said discrimination step and the signal input in said second input step, wherein, when the plural categories are input in said first input step, said discrimination step includes discriminating the category of the object from among the plural categories, and wherein said determination step includes determining the category discriminated in said discrimination step when the approval signal is input in said second input step, and determining the category corresponding to the correction signal when the correction signal is input in said second input step.

11. A method for processing an image of an object, comprising:

a radiation generation step of generating X-rays;

a sensing step of, by using plural kinds of two-dimensional X-ray sensors, obtaining the X-rays generated in said radiation generation step and transmitted through the object, as an image;

a selection step of selecting one of the plural kinds of two-dimensional X-ray sensors;

a calculation step of calculating, from the image obtained in said sensing step with use of the two-dimensional X-ray sensor selected in said selection step, a feature amount to be used to discriminate a category, among plural categories, to which the object belongs;

an input step of inputting the plural categories corresponding to the object; and a discrimination step of discriminating the category of the object based on the feature amount calculated in said calculation step, wherein, when the plural categories are input in said input step, said discrimination step includes discriminating the category of the object from among the plural categories, and wherein said discrimination step includes changing a discrimination rule based on the kind of two-dimensional X-ray sensor selected in said selection step.

12. An apparatus for processing an image of an object, comprising:

radiation generation means for generating X-rays;

a two-dimensional X-ray sensor for obtaining X-rays generated by said radiation generation means and transmitted through the object, as an image;

calculation means for calculating, from the image obtained by said two-dimensional X-ray sensor, a feature amount to be used to discriminate which of plural categories the object belongs to;

discrimination means for discriminating the category of the object based on the feature amount calculated by said calculation means;

input means for inputting a correction signal or an approval signal, corresponding to the category of the object;

determination means for determining the category of the object based on the category discriminated by said discrimination means and the signal input using said input means;

storage means for storing an image processing parameter corresponding to the category of the object; and image processing means for performing an image process on the image by calling out the image processing parameter from said storage means on the basis of the category determined by said determination means, wherein said determination means determines, as the category of the object, the category discriminated by said discrimination means when the approval signal is input, and determines, as the category of the object, the category corresponding to the correction signal when the correction signal is input.

13. An apparatus for processing an image of an object, comprising:

radiation generation means for generating X-rays;

a two-dimensional X-ray sensor for obtaining X-rays generated by said radiation generation means and transmitted through the object, as an image;

calculation means for calculating, from the image obtained by said two-dimensional X-ray sensor, a feature amount to be used to discriminate which of plural categories the object belongs to;

discrimination means for discriminating the category of the object based on the feature amount calculated by said calculation means;

input means for inputting a correction signal or an approval signal, corresponding to the category of the object;

determination means for determining the category of the object based on the category discriminated by said discrimination means and the signal input using said input means, information storage means for storing the feature amount and the category determined by said determination means; and learning means for changing a discrimination algorithm to be used by said discrimination means based on the information stored by said information storage means, wherein said determination means determines, as the category of the object, the category discriminated by said discrimination means when the approval signal is input, and determines, as the category of the object, the category corresponding to the correction signal when the correction signal is input.

* * * * *

UNITED STATES PATENT AND TRADEMARK OFFICE
CERTIFICATE OF CORRECTION

| | |
|---|---|
| PATENT NO. | : 6,911,988 B1 |
| APPLICATION NO. | : 09/717045 |
| DATED | : June 28, 2005 |
| INVENTOR(S) | : Osamu Tsujii |

It is certified that error appears in the above-identified patent and that said Letters Patent is hereby corrected as shown below:

ON COVER PAGE AT (56) UNDER U.S. PATENT DOCUMENTS

"8,313,477" should read --6,313,477--.

SHEET 2

FIG. 2D, "SPAIN" should read --SPINE--.

SHEET 4

FIG. 4, "PHOTPGRAPHING" (four occurrences) should read --PHOTOGRAPHING--.

SHEET 5

FIG. 5A, "SPAIN" (two occurrences) should read --SPINE--; and "ANCON" (two occurrences) should read --ELBOW--; and
FIG. 5D, "ANCON" (two occurrences) should read --ELBOW--.

SHEET 6

FIG. 6, "ANCON" should read --ELBOW--.

SHEET 10

FIG. 12A, "RESGION" should read --REGION--; and "VERTEBRA" should read --VERTEBRAE--;
FIG. 12C, "SPAIN" should read --SPINE--; and
FIG. 12D, "SPAIN" should read --SPINE--.

SHEET 11

FIG. 13A, "RESGION" should read --REGION--; and "VERTEBRA" should read --VERTEBRAE--;
FIG. 13B, "SPAIN" (two occurrences) should read --SPINE--;
FIG. 13C, "SPAIN" should read --SPINE--; and
FIG. 13D, "SPAIN" should read --SPINE--.

UNITED STATES PATENT AND TRADEMARK OFFICE
CERTIFICATE OF CORRECTION

PATENT NO. : 6,911,988 B1
APPLICATION NO. : 09/717045
DATED : June 28, 2005
INVENTOR(S) : Osamu Tsujii It is certified that error appears in the above-identified patent and that said Letters Patent is hereby corrected as shown below:

<u>COLUMN 2</u>

Line 7, "parameters" should read --parameter--;
Line 8, "graduation" should read --gradation--;
Line 9, "parameters" should read --parameter--; and
Line 42, "histogram" should read --histogram or--.

<u>COLUMN 12</u>

Line 13, "angel θ" should read --angle θ--.

<u>COLUMN 14</u>

Line 18, "displays" should read --displayed--.

<u>COLUMN 16</u>

Line 18, "displays" should read --displayed--.

<u>COLUMN 19</u>

Line 3, "form" should read --from--.

Signed and Sealed this

Twenty-sixth Day of June, 2007

JON W. DUDAS
*Director of the United States Patent and Trademark Office*